(12) United States Patent
Samadani et al.

(10) Patent No.: US 10,201,274 B2
(45) Date of Patent: Feb. 12, 2019

(54) EYE TRACKING SYSTEM WITH BIOMETRIC IDENTIFICATION

(71) Applicant: OCULOGICA INC, New York, NY (US)

(72) Inventors: Rosina Samadani, New York, NY (US); Daniel O. Sanderson, New Richmond, WI (US)

(73) Assignee: OCULOGICA INC, New York, NY (US)

( * ) Notice: Subject to any disclaimer, the term of this patent is extended or adjusted under 35 U.S.C. 154(b) by 0 days.

(21) Appl. No.: 15/786,759

(22) Filed: Oct. 18, 2017

(65) Prior Publication Data

US 2018/0110410 A1    Apr. 26, 2018

Related U.S. Application Data

(60) Provisional application No. 62/410,754, filed on Oct. 20, 2016.

(51) Int. Cl.
*A61B 3/00* (2006.01)
*A61B 5/00* (2006.01)
(Continued)

(52) U.S. Cl.
CPC ............ *A61B 3/113* (2013.01); *A61B 3/0041* (2013.01); *A61B 3/0083* (2013.01); *A61B 5/004* (2013.01);
(Continued)

(58) Field of Classification Search
CPC .......... G06F 21/32; G06F 19/00; G06F 21/83; G06F 2221/2139; G06F 3/017; G06F 19/3406; G06F 19/3462; G06F 21/31
(Continued)

(56) References Cited

U.S. PATENT DOCUMENTS 5,961,448 A    10/1999   Swenson et al.
7,496,174 B2 *  2/2009   Gertner ................ A61N 5/1017
                                                    378/65
(Continued)

FOREIGN PATENT DOCUMENTS

WO    WO2013148557    10/2013
WO    WO2014204904    12/2014

OTHER PUBLICATIONS

Samadani et al., U.S. Appl. No. 15/716,826, filed Sep. 27, 2017, 35 pages.

(Continued)

*Primary Examiner* — Mark S Blouin
(74) *Attorney, Agent, or Firm* — Merchant & Gould P.C.

(57) ABSTRACT

A method for measuring eye tracking in a patient and capturing ocular biometric identifying information from the patient may involve: displaying a video to the patient on a stimulus screen of an eye tracking and biometric identification system; tracking movement of the patient's eyes during display of the video via an eye tracking camera of the eye tracking and biometric identification system; capturing ocular biometric identifying information from the patient with an ocular biometric capture device of the eye tracking and biometric identification system; generating, with a computer processor of the eye tracking and biometric identification system, a score representing an ability of the patient's eyes to track the video; and confirming, with the computer processor, an identity of the patient, based on the captured ocular biometric identifying information.

20 Claims, 5 Drawing Sheets

(51) Int. Cl.
*A61B 5/16* (2006.01)
*A61B 3/113* (2006.01)
*A61B 5/1171* (2016.01)

(52) U.S. Cl.
CPC .......... *A61B 5/0077* (2013.01); *A61B 5/1171* (2016.02); *A61B 5/163* (2017.08); *A61B 5/4064* (2013.01); *A61B 5/168* (2013.01); *A61B 5/40* (2013.01); *A61B 5/7264* (2013.01); *A61B 5/7475* (2013.01); *A61B 2503/12* (2013.01)

(58) Field of Classification Search
USPC ....................................................... 340/5.82
See application file for complete search history.

(56) References Cited

U.S. PATENT DOCUMENTS

| | | | | |
|---|---|---|---|---|
| 7,703,921 B2 * | 4/2010 | Dick | ...................... | A61B 3/113 351/205 |
| 7,792,249 B2 * | 9/2010 | Gertner | ................... | A61F 9/008 378/65 |
| 8,732,795 B2 | 5/2014 | Skeel et al. | | |
| 9,101,312 B2 * | 8/2015 | Waldorf | ................. | A61B 3/032 |
| 9,229,227 B2 * | 1/2016 | Border | ............... | G02B 27/0093 |
| 9,439,592 B2 | 9/2016 | Stack et al. | | |
| 9,459,451 B2 * | 10/2016 | Saarikko | ............ | G02B 6/02085 |
| 9,642,522 B2 | 5/2017 | Samadani et al. | | |
| 2001/0056359 A1 | 12/2001 | Abreu | | |
| 2013/0144185 A1 | 6/2013 | Fuller | | |
| 2013/0208952 A1 | 8/2013 | Auchinleck | | |
| 2013/0278899 A1 | 10/2013 | Waldorf | | |
| 2015/0190050 A1 | 7/2015 | Samadani et al. | | |
| 2015/0326570 A1 * | 11/2015 | Publicover | .............. | G06F 21/64 726/4 |
| 2016/0278716 A1 | 9/2016 | Samadani | | |
| 2017/0091392 A1 | 3/2017 | White et al. | | |
| 2017/0135577 A1 * | 5/2017 | Komogortsev | ...... | A61B 5/1103 |
| 2017/0172408 A1 | 6/2017 | Samadani et al. | | |
| 2017/0364732 A1 * | 12/2017 | Komogortsev | .... | G02B 27/0093 |
| 2017/0367633 A1 | 12/2017 | Samadani et al. | | |
| 2018/0116512 A1 | 5/2018 | Bitoun | | |

OTHER PUBLICATIONS

Samadani et al., U.S. Appl. No. 62/403,440, filed Oct. 3, 2016, 18 pages.
Samadani et al., U.S. Appl. No. 62/410,754, filed Oct. 20, 2016, 11 pages.
Samadani et al., U.S. Appl. No. 62/558,069, filed Sep. 13, 2017, 43 pages.

* cited by examiner

EYE TRACKING SYSTEM WITH BIOMETRIC IDENTIFICATION

CROSS-REFERENCE TO RELATED APPLICATIONS

This application claims priority to U.S. Provisional Patent Application Ser. No. 62/410,754, entitled "Apparatus for Biometric Identification Within An Eye-Tracking Apparatus For Neuro-Diagnosis," filed Oct. 20, 2016, the full disclosure of which is hereby incorporated by reference.

This application also hereby incorporates by reference: U.S. Pat. No. 9,642,522; U.S. Patent Application Pub. Nos. 2016/0278716 and 2017/0172408; and U.S. patent application Ser. No. 15/716,826 titled "Method for Detecting Glaucoma," filed Sep. 27, 2017, and 62/558,069, titled "Eye Tracking System," filed Sep. 13, 2017. The above-listed patents and applications may be referred to collectively below as "The Incorporated References." The above-listed patents and applications, as well as all publications, patent applications, patents and other reference material mentioned in this application, are hereby incorporated by reference in their entirety.

TECHNICAL FIELD

This application is directed to medical devices, systems and methods. More specifically, the application is directed to devices, systems and methods for providing eye tracking and biometric identification.

BACKGROUND OF THE INVENTION

Many central nervous system injuries and abnormalities can be challenging to diagnose and localize within the nervous system. The assignee of the present application has developed methods and systems that use eye tracking measurement to help diagnose and/or localize a number of different central nervous system injuries and abnormalities, such as but not limited to increased intracranial pressure (ICP), concussion, traumatic brain injury (TBI), reduced or impaired cranial nerve function, and the like. Some of these methods and systems are described in the Incorporated References.

BRIEF SUMMARY

The present application is directed to a system and method that combines eye tracking capabilities with ocular biometric identification of an individual. Using the system and method, biometric identification may be performed before or during an eye tracking session. Identification of the patient may be performed by a cloud-based biometric service. In various embodiments, the biometric identification component of the system may be incorporated into, or added to, any suitable eye tracking system, such as but not limited to the eye tracking systems described in the Incorporated References.

These and other aspects and embodiments are described in greater detail below, in reference to the attached drawing figures.

DETAILED DESCRIPTION OF THE INVENTION

The assignee of the present patent application has developed eye tracking devices, systems and methods that may be used to track the movement of a patient's pupils over time as they follow a video moving across a screen and measure metrics such as distance traveled over time and the ability to coordinate eye movements. Cranial Nerve III and VI palsies, for example, may be identified using this system and method, which includes at least one computer processor that employs an algorithm to perform diagnostic calculations. These devices, systems and methods are described more fully in the Incorporated References. The present application uses the same technology, method and algorithm to provide a non-invasive eye tracking methodology to measure ICP, and combines that technology and methodology with a device and method for biometric identification of the patient.

Figure 1A:
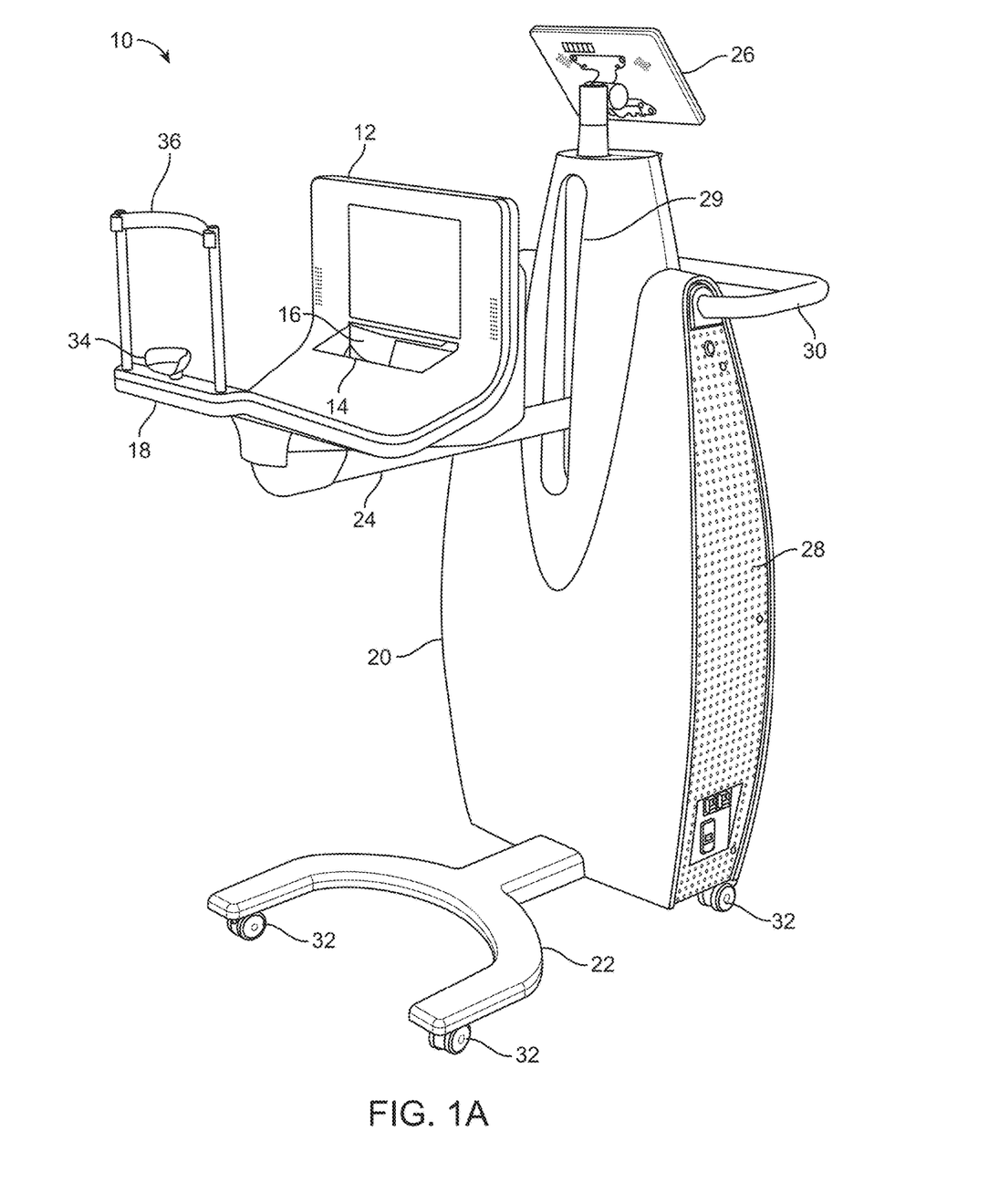
FIGS. 1A-1C are patient-facing, side, and technician-facing views, respectively, of a system for measuring eye tracking, according to one embodiment.
Figure 1B:
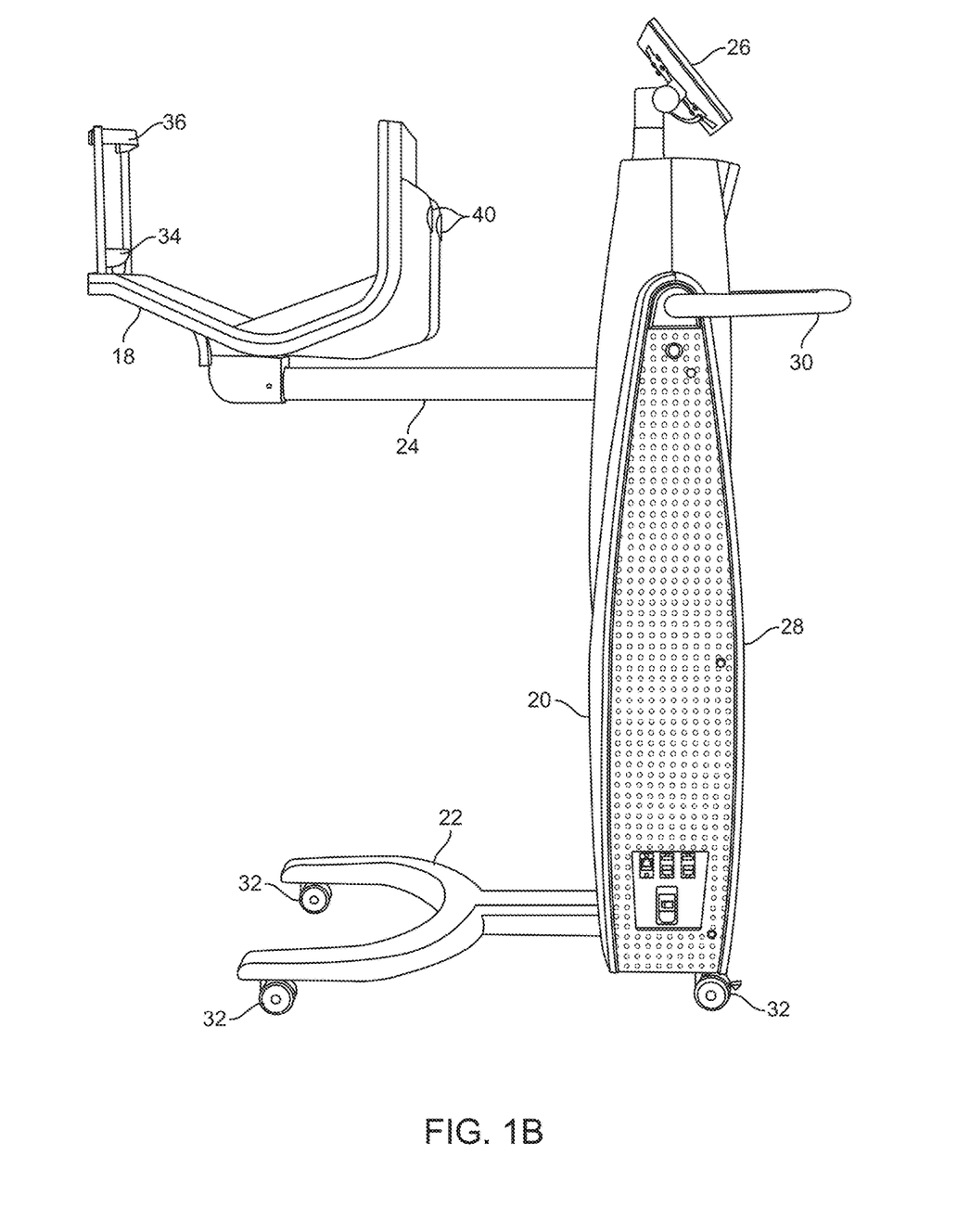
Figure 1C:
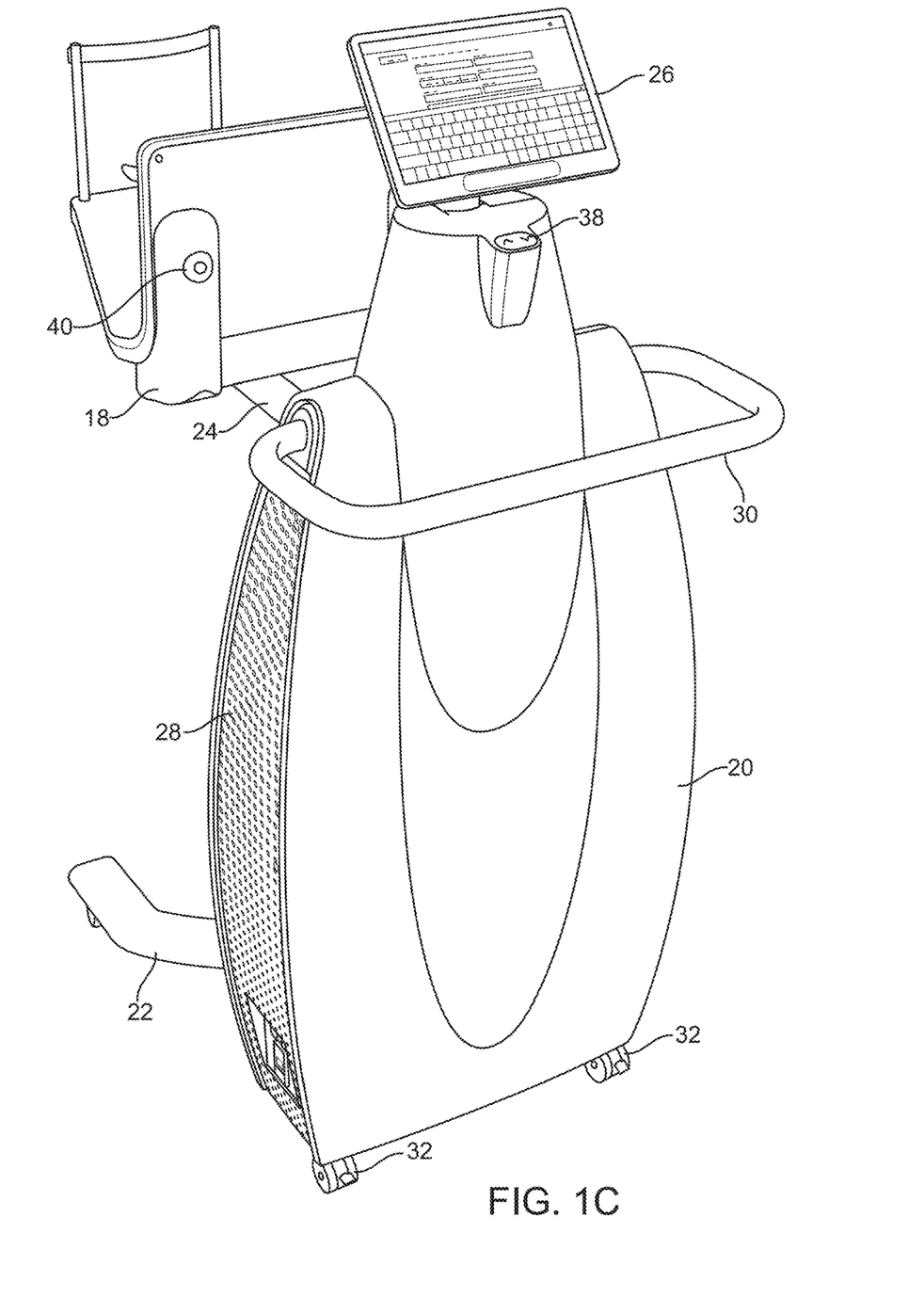

Referring to FIGS. 1A-1C, an eye tracking, biometric identification and diagnostic system 10 is illustrated, according to one embodiment. The eye tracking portion of system 10 is described in further detail in U.S. Provisional Patent Application Ser. No. 62/558,069, which was previously incorporated by reference. System 10 is used to track a patient's eye movement and diagnose one or more eye movement abnormalities. In some embodiments, system 10 includes at least one processor, which may further analyze data related to the eye movement abnormalities to help diagnose and/or localize a neurological injury or abnormality, such as but not limited to increased ICP, concussion, TBI, or reduced or impaired cranial nerve function. In use, a stimulus video is presented on system's 10 LCD stimulus screen 12, and the patient's eye movement is tracked over time by an infrared eye tracking camera 14. Fixed orientation of the patient's head, relative to the stimulus screen 12 and camera 14, is ensured by a head rest assembly 18, which adjusts to a seated or supine patient. System 10 is operated from a touchscreen interface 26. System 10 is coupled together via a wheeled chassis 20 suitable for wheeling to the examination location.

Chassis 20 includes two main parts: a main column 28 supported by a base 22, and a head rest assembly 18. Head rest assembly 18 is supported on an arm 24, which can be raised and lowered using an electrically-driven elevator in main column 28, controlled by an up/down button 38 (FIG. 1C). Arm 24 moves up and down through a vertical slot 29 (FIG. 1A) in main column 28. Four locking castors 32 in base 22 allow the entire unit to be moved, with base 32 being sized to fit underneath a patient bed or gurney. A handle 30 on main column 28 is used to push and/or pull system 10 into place.

In one embodiment, main column 28 houses two computers, a power supply, the elevator mechanism, an isolation transformer, and other electrical parts, none of which is visible in the figures. Operator touchscreen interface 26 (also called "operator console 26" herein) is located on main column 28.

Head rest assembly 18 includes a chin rest 34 and a forehead rest 36, to stabilize the patient's head, stimulus screen 12, an optical mirror 16 used to fold the optical path allowing for more compact casing, and a high-speed eye tracking camera 14. The entire head rest assembly 18 can be rotated in the horizontal plane 90 degrees in either direction, for a total horizontal rotation of 180 degrees, and up to 90 degrees in the vertical direction downward to accommodate supine patients. In one embodiment, there are several discrete positions within the vertical rotation where head rest assembly 18 locks into place. Buttons 40 on the back of head rest assembly 18 activate solenoids, so assembly 18 can be rotated vertically and then locked.

A standard 110-volt medical grade cord may provide power to system's 10 elevator mechanism and a 400-watt power supply. The power supply provides regulated DC power to the computers, as well as the solenoid controls in head rest assembly 18.

System 10 includes two computers, which are housed in main column 28 of chassis 20 and thus not visible in the figures. A camera computer, which may be provided by the same manufacturer as the manufacturer of camera 14, may run the real-time software for camera 14 under a real-time operating system. It detects eye motion events, such as saccades, blinks, and fixations, and computes the gaze coordinates for each eye at 500 Hz, storing the raw data until it is needed by the application. The application computer may be a small form-factor PC that runs a system application for system 10. The system application provides the user interface, controls the logic flow, displays the stimulus video, processes the raw data from the camera computer, and stores results in persistent storage.

The user interacts with the system application through touchscreen interface 26. Stimulus screen 12 (the second monitor on system 10) displays the stimulus media to the patient. Two built-in speakers provide the audio for the stimulus media.

In some embodiments, the processor(s) in system 10 is configured to generate a score describing a patient's eye tracking ability. For example, in one embodiment, system 10 generates a score ranging from 0-20, where the score is interpreted as a binary classification for eye movement abnormalities, and where anything equal to or greater than 10 is a positive result (abnormality present) and everything below 10 is negative (no abnormality). The system's 10 operating algorithm identifies eye tracking abnormalities and computes the score.

In one embodiment, eye tracking camera 14 is an EyeLink 1000 Plus USB (SR Research, Ottawa, Canada) and is used to capture the eye movements of the patient. Camera 14 captures 500 frames of gaze data per second for each eye, with an average accuracy of 0.25 to 0.5 degrees. The illuminators are infrared, and it uses dark pupil eye tracking, in which the infrared sources are offset from camera 14. This technique typically provides better results across ethnicities and varied lighting conditions. The gaze tracking ranges up to 32 degrees horizontally and 25 degrees vertically. The distance between the subject's eyes and the camera is 52 cm. The specifications for camera 14, as provided by the vendor, are shown in Table 1.

TABLE 1

EyeLink Camera Specifications

| Spec | Description |
| --- | --- |
| Average accuracy of gaze coordinate data | Down to 0.15 degrees (0.25 degrees to 0.5 degrees typical) |
| sampling rate | Binocular: 250, 500 hz |

TABLE 1-continued

EyeLink Camera Specifications

| Spec | Description |
| --- | --- |
| End-to-end sample delay | m < 1.8 msec, sd < 0.6 msec @ 1000 hz |
| Blink/occlusion recovery | m < 1.8 msec, sd < 0.6 msec @ 1000 hz |
| Spatial resolution | <0.01 degrees rms |
| Eye tracking principle | Dark pupil - corneal reflection |
| Pupil detection models | Centroid or ellipse fitting |
| Pupil size resolution | 0.2% of diameter |
| Gaze tracking range | 32 degrees horizontally, 25 degrees vertically |
| Allowed head movements without accuracy reduction | ±25 mm horizontal or vertical6, ±10 mm depth |
| Optimal camera-eye distance | Between 40-70 cm |
| Glasses compatibility | The user must remove their glasses to use the system |
| On-line event parsing | Fixation/saccade/blink/fixation update |
| Real-time operator feedback | Eye position cursor or position traces. Camera images and tracking status. |

Eye Tracking Computer

As mentioned above, in one embodiment, camera 14 is driven by a dedicated real-time computer running the QNX operating system. The specifications for this eye tracking computer are shown in Table 2.

TABLE 2

EyeLink Computer Specifications

| Spec | Description |
| --- | --- |
| Design | Pico form factor; 8-layer SBC PCB size: 100 mm × 72 mm |
| Embedded CPU | Intel Braswell SoC CPU |
| Memory | Onboard 4 GB unbuffered DDR3L 1600 MHz DRAM |
| Expansion slot | 1 full-size mini-PCIE slot |
| Storage | SATA III port M.2 M-key 2242 slot |
| LAN chip | Integrated with Intel i211AT PCI-E Gigabit LAN chip Support fast Ethernet LAN function of providing 10/100/1000 Mbps Ethernet data transfer rate |
| Audio chip | Realtek ALC662 2-CH HD audio codec integrated Audio driver and utility included |
| BIOS | 64 Mbit flash ROM |
| Rear I/O | 12 V DC-in power jack USB 3.0 port (2) Display port RJ-45 LAN port |
| Internal I/O | 2-pin internal 12 V DC-in power connector SATA power-out connector Front panel audio header 9-pin USB 2.0 header Serial port header (2) Front panel header LAN LED activity header LVDS header LVDS inverter |

System Application Computer

As mentioned above, in one embodiment, the system application runs on a mini-ITX board running Windows 10 Pro, configured as a kiosk device. The specifications are shown in Table 3.

TABLE 3

System Application Computer Specifications

| Spec | Description |
| --- | --- |
| Design | Mini ITX form factor |
| CPU | Intel i7 (speed, etc TBD) |
| Chipset | Intel H170 |
| Memory | 16 GB dual channel DDR4 |

TABLE 3-continued

System Application Computer Specifications

| Spec | Description |
|---|---|
| Expansion slot | PCI Express 3.0 × 16 slot |
| | Vertical half-size mini-PCI Express slot |
| Graphics | Intel HD graphics, dual graphics output, DVI/HDMI max resolution to 4K × 2K |
| Additional graphics | Invidia GeForce 210, DVI/VGA/DisplayPort max resolution to 2560 × 1600 |
| Audio | 7.1 CH HD audio |
| LAN | Intel 1219V (gigabit LAN) |
| | Realtek RTL8111H (gigabit LAN) |
| Rear I/O | PS/2 mouse/keyboard port |
| | DVI port |
| | HDMI port |
| | USB 2.0 ports (2) |
| | USB 3.0 ports (6) |
| | RJ-45 LAN ports (2) |
| | HD audio jack |
| Storage | SATA 3 256 GB SSD |
| BIOS | 128 MB AMI UEFI legal BIOS |
| Certifications | FCC, CE, WHQL |

Stimulus Display

Stimulus screen 12, according to one embodiment, is used to display a video that may last any suitable length of time, such as 220 seconds in one embodiment. In one embodiment, the only purpose of stimulus screen 12 is to display the visual stimulus. The video may be one of several predetermined videos. These videos may include music videos, clips from children's movies, sports clips, talent performances, "reality TV" clips, etc. The choice of videos may be designed to appeal to a broad group of subjects. Users of the device may choose which video to display or may ask the patient which one they would like to watch. Additional media selections may be downloaded via a UBS drive, for example. In one embodiment, the video aperture is square, with each side being approximately ¼ the width of the visible display. The trajectory of the displayed video around stimulus screen 12 follows a predefined discrete path, such as 5 cycles along the perimeter of stimulus screen 12 with a velocity of 10 seconds per side, according to one embodiment. In one embodiment, stimulus screen 12 is an GeChic 1303 monitor, with the specifications shown below in Table 4.

TABLE 4

Stimulus Screen Specifications

| Spec | Description |
|---|---|
| Aspect ratio | 1.78:1 |
| Maximum resolution | 1920 × 1080 |
| Screen size | 13.3 inches |
| Display type | LED |
| Viewing angle | 89°/89°/89°/89° |
| Contrast ratio | 700:1 |
| Power input | 5 V, 2.0 A |

Touchscreen Interface

Touchscreen interface 26 (which may also be referred to as an "operator console" or simply "touchscreen") is used by the technician to interact with the system application. In the pictured embodiment, touchscreen interface 26 includes only a touch screen display, meaning that there is no keyboard or other input device. Of course, alternative embodiments may include a keyboard or other input device(s). In one embodiment, touchscreen interface 26 may be a Mimo UM-1080CH-G, with the specifications set forth below in Table 5.

TABLE 5

Touchscreen Interface Specifications

| Spec | Description |
|---|---|
| Capacitive touchscreen | Yes |
| Maximum resolution | 1280 × 800 |
| Screen size | 10.1 inches |
| Viewing angle | 170° × 170° |
| Contrast ratio | 800:1 |
| Power input | 6 W |

Head Rest Assembly

Chin rest 34 and forehead rest 36 are used to stabilize the user's head and maintain appropriate distance from stimulus screen 12 during eye tracking. Chin rest 34 may be made from the non-toxic, non-hazardous biodegradable plastic Bakelite resin (polyoxybenzylmethylenglycolanhydride), and forehead rest 36 may be constructed from aluminum covered with a thin EPDM (ethylene propylene diene terpolymer) foam pad blended with neoprene and SBR (styrene-butadiene rubber) pad with closed-cell construction, to resist liquid, solid, and gas absorbance. Both surfaces may be wiped using sterile alcohol swabs before and after each use.

System Calibration

The calibration information below in Table 6 applies to the components of system, according to one embodiment.

TABLE 6

System Calibration

| Component | Calibration notes |
|---|---|
| Eye tracking camera 14 | A focus knob on the bottom of the unit adjusts focus. Once it is set, it generally does not need any adjustment unless the knob is accidentally jarred. The user guide provides instructions for adjusting focus. Gaze point calibration is not required. System 10 uses camera's 14 built-in default calibration for calculating gaze points from pupil detection and corneal reflection measurements. |
| Stimulus display 12 | Stimulus display 12 is surrounded by bezels to reduce the size of display 12 to effectively be 4:3 instead of 1.78:1. The software uses calibration information stored in the device configuration file to determine what part of the display is actually visible to the user. The configuration, once set, does not change since the bezels and display are fixed. These configuration parameters will be set at the factory before being shipped to the end user. |
| Operator console 26 | The aspect ratio will be set when the unit is assembled. No additional calibration by the user is needed. |
| Computers | The computers perform a boot sequence upon startup that will run diagnostic procedures to ensure correct operation. No additional calibration of the computers is necessary. |
| Head rest assembly 18 rotation | At assembly time, the head rest assembly 18 rotation limits are set and fixed into place. No additional calibration is needed. |
| Chin rest 34 and forehead rest 36 | The user should use an alcohol wipe before and after each patient in order to sterilize the parts of the device that come in contact with the patient. Instructions for this are included in the user guide. |
| Elevator | At assembly time, the elevator height limits are set and fixed into place. No additional calibration is needed. The elevator is not expected to require any maintenance during the normal lifetime of the device. |
| Optical mirror 16 | Dust or dirt may accumulate in the camera/mirror bay of head rest assembly 18. User guide instructions provide information about how to remove the debris using compressed air if needed. |

Principle of Operation

System 10 measures a patient's eye tracking while watching a video move around stimulus screen 12 and then analyzes the data from the eye tracking measurements, using an algorithm, to extract clinically relevant eye measures by using temporal assessment. The patient watches a video moving inside an aperture with a set trajectory for 220 seconds (in one embodiment) at a fixed distance from stimulus screen 12. The position of each pupil is recorded over time elapsed, as the video travels on its time course, enabling detection of impaired ability to move the eyes relative to time and therefore relative to each other. The algorithm inputs are measurements of the individual (left and right) eye-movements, averaged over the 5 cycles that the eyes move while watching the 220-second video that plays in an aperture moving around screen 12. In one embodiment, the algorithm output is a "BOX Score," calculated by multiplying multiple constants with different individual parameters, and summing those factors.

System Computer Processing Overview

Central to the operation of system 10 is how the software processes raw gaze data from the eye tracking camera and calculates a BOX score. An overview of this process is outlined below.

1. During a tracking, system 10 collects 220 seconds of binocular gaze data at 500 Hz as the patient watches the video stimulus go around screen 12 five times. The trajectory is as follows:
    a. The stimulus starts in the upper left corner and remains stationary for 10 seconds.
    b. The stimulus moves around the outer edges of the stimulus screen in a clockwise fashion, taking ten seconds for each side or 40 second for each cycle. The stimulus makes five cycles plus one extra side along the top for a total of 220 seconds.
2. The first and last ten seconds of data are discarded.
3. The processing first removes blink data. These data become "NaN's" (not a number) in the processing and are ignored in all subsequent processing.
4. Next, the gaze data are normalized, and several dozen metrics are computed from the normalized data, which characterize the patient's tracking. Some of the metrics are conjugate values that evaluate the differences between the left and right eye.
5. The most correlated metrics are then fed into a polynomial formula that produces a BOX score between 0 and 20. Scores less than 10 are considered normal.
6. The algorithm also computes a quality score (1 to 10 with 10 being the best) based on the percentage of NaN's that were in the raw data.

Figure 2:
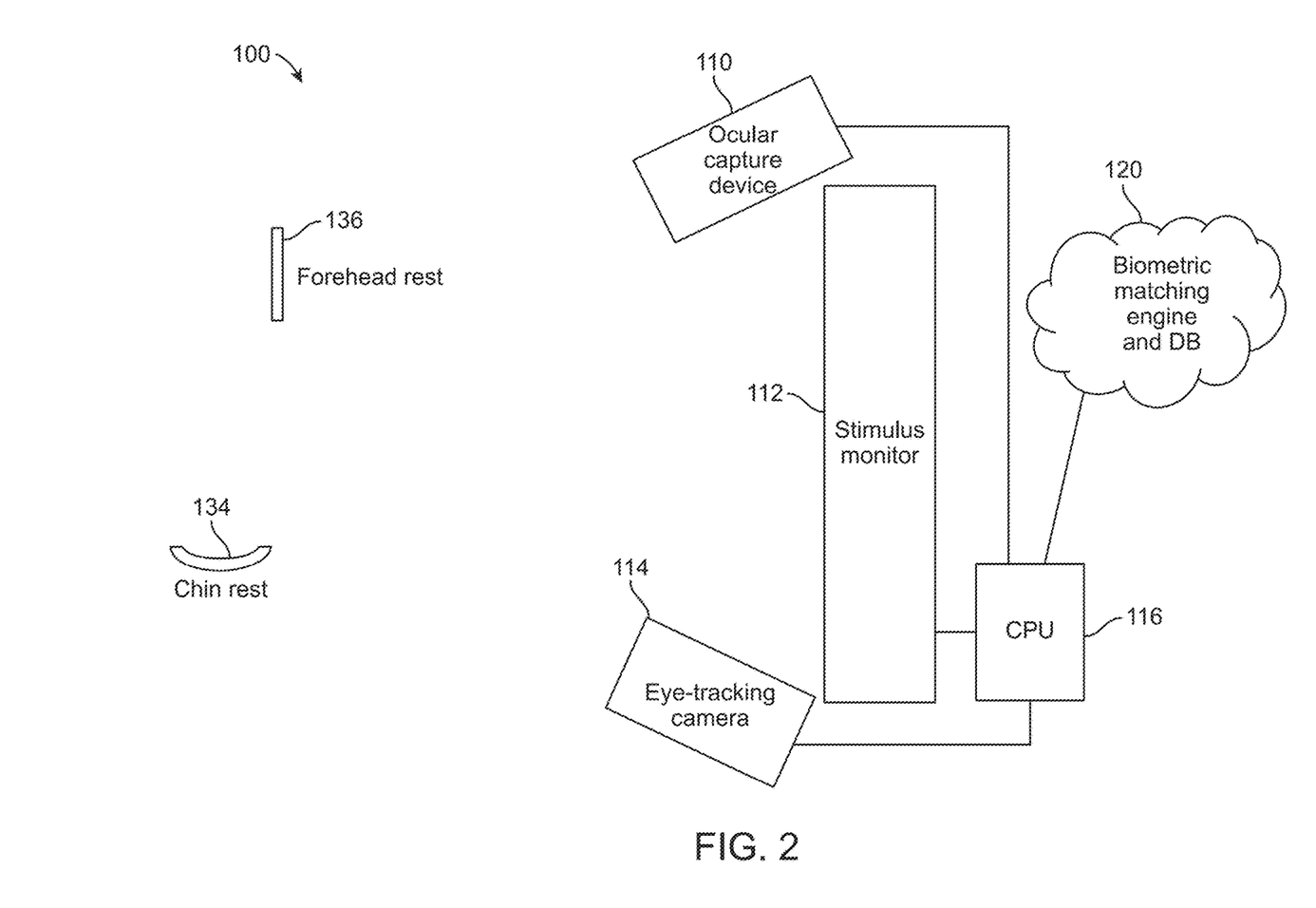
FIG. 2 is side-view diagram of an eye tracking system that includes an ocular capture device for biometric identification, according to one embodiment.

Referring now to FIG. 2, a diagrammatic representation of a combined eye tracking and biometric identification system 100 is provided. In this embodiment, system 100 includes an ocular biometric capture device 110, a stimulus monitor 112, an eye tracking camera 114, a central processing unit (CPU) 116, a chin rest 134, a forehead rest 136, and a biometric matching engine and database 120. Any or all of the details regarding the eye tracking features and components of system 100 may be the same as, or similar to, those described above in relation to system 10 and FIGS. 1A-1C. During use, the patient's face is stabilized in chin rest 134 and forehead rest 136, at a precise distance from stimulus monitor 112. Eye tracking camera 114 is positioned just below stimulus monitor 112 and captures images from the eyes. Ocular biometric capture device 110 is positioned just above stimulus monitor 112 and captures biometric data from the eyes. In an alternative embodiment, eye tracking camera 114 may be configured to capture ocular biometric data from the patient, thus eliminating the need for a separate ocular capture device 110. Central processing unit 116 controls the display of the stimulus media, eye tracking camera 114 and ocular biometric capture device 110. Central processing unit 116 also communicates with cloud-based biometric matching engine and database 120.

Figure 3:
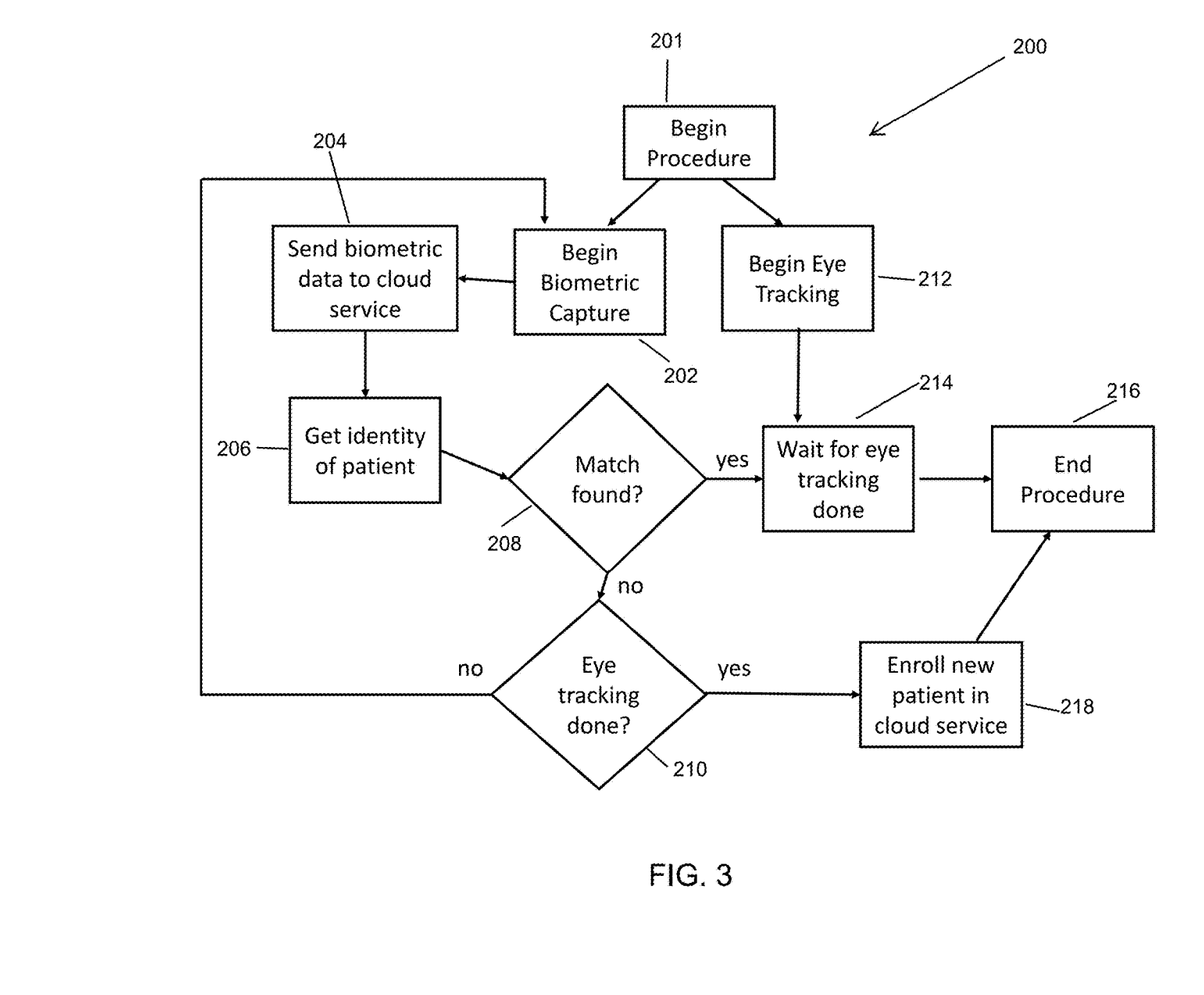
FIG. 3 is a flow diagram, illustrating a method for eye tracking and biometric identification, according to one embodiment.

Referring now to FIG. 3, a flow diagram of a combined eye tracking and biometric identification method 200 is provided. In the illustrated embodiment, biometric identification and eye tracking are shown as if performed in parallel. This may be the case in some embodiments, but according to various embodiments, it is possible to perform biometric identification before, during and/or after eye tracking. In other words, method 200 is not limited to one particular timing or sequence.

In the illustrated embodiment, at the beginning of the procedure 201, two threads of execution are initiated, one that begins an ocular biometric data capture method 202 and one that begins an eye tracking method 212. Eye tracking method 212 may be the same as, or similar to, the methods described above. In FIG. 3, the details of eye tracking method 212 are not illustrated and instead are shown simply as eye-tracking session complete 214, which is typically signaled by the end of the stimulus video. Biometric method 202 involves capturing an ocular biometric sample and sending it to a cloud-based biometric identification service 204, for example including matching engine and database 120 (FIG. 2). The service attempts to match the biometric sample with a record in the biometric data 206. If a match is found 208, biometric method 202 associates the patient with the current eye-tracking session, and waits until the eye tracking session is complete 214. If a match is not found 210 and the eye tracking is not complete, another biometric sample is taken 202 and sent to the cloud-based service 204. This process continues until either a match is found or the eye-tracking session is complete. Sending multiple biometric samples to the cloud-based service decreases the chance of the ultimate result being that no match is found, even though the patient is enrolled. If the eye tracking session completes without a match being found, the patient's demographic data is requested, linked to the biometric sample(s), and sent to the cloud-based service as a new enrollment 218. This method 200 is just one embodiment, and variations may be made without departing from the scope of the disclosure. For example, alternative embodiments may include fewer steps, greater numbers of steps and/or different ordering of steps.

The foregoing is believed to be a complete and accurate description of various embodiments of a system and method for assessing glaucoma in a patient. The description is of embodiments only, however, and is not meant to limit the scope of the invention set forth in the claims.

We claim:

1. A system for measuring eye tracking in a patient and identifying the patient by capturing ocular biometric identifying information from the patient and matching the captured ocular biometric identifying information with a record of biometric data, the system comprising:
    a head rest assembly for stabilizing the patient's head;
    an operator console for receiving user inputs to control the system;
    a stimulus screen on the headrest assembly, for displaying a video to the patient;
    an eye tracking camera on the headrest assembly;
    an ocular biometric capture device coupled with the headrest assembly, for capturing the ocular biometric identifying information from the patient;
    a central processing unit for controlling the stimulus screen, data processing and other functions of the system; and a biometric matching engine and database in communication with the central processing unit for matching the captured ocular biometric identifying information with a record of biometric data.

2. The system of claim 1, wherein the eye tracking camera is positioned below the stimulus screen, and the ocular biometric capture device is attached to the head rest assembly above the stimulus screen.

3. The system of claim 1, wherein the ocular biometric capture device is separate from the eye tracking camera.

4. The system of claim 1, wherein the ocular biometric capture device is incorporated into the eye tracking camera.

5. The system of claim 1, wherein the biometric matching engine and database comprises ocular biometric scans of multiple patients, and wherein the central processing unit is configured to check the captured ocular biometric identifying information from the patient against the ocular biometric scans of the multiple patients.

6. The system of claim 1, further comprising at least one light source for illuminating the patient's eyes, wherein the ocular biometric capture device is configured to capture reflections of light emitted by the at least one light source after they are reflected by the patient's eyes.

7. The system of claim 6, wherein the at least one light source is selected from the group consisting of an infrared light source, a near infrared light source and a visible light source.

8. The system of claim 7, wherein the ocular biometric capture device is selected from the group consisting of an infrared camera, a near infrared camera, and a visible light camera.

9. The system of claim 6, wherein the at least one light source comprises a light emitting diode.

10. A method for measuring eye tracking in a patient and identifying the patient by capturing ocular biometric identifying information from the patient and matching it with a record of biometric data, the method comprising:
adjusting a vertical height of a head rest assembly of an eye tracking system;
displaying a video to the patient on a stimulus screen on the head rest assembly of the eye tracking system, according to a video selection made by the patient;
tracking movement of the patient's eyes during display of the video via an eye tracking camera on the head rest assembly of the eye tracking system;
capturing ocular biometric identifying information from the patient with an ocular biometric capture device coupled with the head rest assembly of the eye tracking system;
generating, with a computer processor of the eye tracking system, a score representing an ability of the patient's eyes to track the video; and
confirming, with the computer processor, an identity of the patient, by matching the captured ocular biometric identifying information with the record of biometric data.

11. The method of claim 10, further comprising:
receiving user information input by a user via a touchscreen interface of the eye tracking system;
receiving patient information input by the user via the touchscreen interface; and
receiving a video selection from the patient via the stimulus screen of the eye tracking system.

12. The method of claim 10, wherein displaying the video to the patient comprises displaying images associated with a time stamp driven by a system clock.

13. The method of claim 10, wherein confirming the identity of the patient comprises comparing, with the computer processor, the captured ocular biometric identifying information with multiple patient scans stored on a database operatively coupled with the computer processor.

14. The method of claim 13, wherein the database is located in the cloud, and wherein the method further comprises transmitting the captured ocular biometric identifying information to the database in the cloud.

15. The method of claim 14, further comprising using a cloud-based computing service to search the database.

16. The method of claim 15, wherein the captured ocular biometric identifying information, if returned from the cloud-based computing service, causes an association to be established between the patient and a previously enrolled patient.

17. The method of claim 15, wherein if the captured ocular biometric identifying information is not returned from the cloud-based computing service, the computer processor causes the captured ocular biometric identifying information to be enrolled in the cloud-based computing service, unless the eye-tracking session is still ongoing, wherein a new biometric sample is captured and sent to the cloud-based service.

18. The method of claim 10, wherein the capturing and confirming steps are performed before the video is displayed.

19. The method of claim 10, wherein the capturing and confirming steps are performed while the video is displayed.

20. The method of claim 10, wherein the ocular biometric capture device is incorporated into the eye tracking camera.

* * * * *